United States Patent [19]

Masaoka

[11] Patent Number: 4,845,078
[45] Date of Patent: Jul. 4, 1989

[54] METHOD FOR TREATING HEMATOPOIETIC DISEASES

[75] Inventor: Tohru Masaoka, Osaka, Japan

[73] Assignees: Green Cross Corporation, Osaka; Morinaga Milk Industry Co., Ltd., Tokyo, both of Japan

[21] Appl. No.: 894,598

[22] Filed: Aug. 8, 1986

[30] Foreign Application Priority Data

Aug. 9, 1985 [JP] Japan .................. 60-174325

[51] Int. Cl.$^4$ .................. A61K 37/02; A61K 35/22
[52] U.S. Cl. .................. 514/8; 424/99; 424/100
[58] Field of Search .................. 424/99, 100; 530/395, 530/834; 514/8

[56] References Cited

U.S. PATENT DOCUMENTS

| | | | |
|---|---|---|---|
| 3,991,182 | 11/1976 | Spitler et al. | 424/101 |
| 4,230,697 | 10/1980 | Nishida et al. | 514/8 |
| 4,275,056 | 6/1981 | Takaku et al. | 514/8 |
| 4,342,828 | 8/1982 | Takaku et al. | 514/8 |
| 4,482,485 | 11/1984 | Funakoshi et al. | 424/99 |
| 4,540,574 | 9/1985 | Pierpaoli et al. | 424/95 |

FOREIGN PATENT DOCUMENTS 2016477 9/1979 United Kingdom .
2058081 4/1981 United Kingdom .

OTHER PUBLICATIONS

Wells et al., "Bone Marrow Transplantation", in *Basic & Clinical Immunology*, 5th Ed., Ch. 24, pp. 484–488, 1984.

Journal of chromatography, vol. 283, 1984, pp. 459–461, Elsevier Science Publishers, Amsterdam, NL; P. V. Byrne.

Chemical Abstracts, vol. 102, No. 3, Jan. 21, 1985, p. 487, Abst. No. 22216b.

*Primary Examiner*—Johnnie R. Brown
*Assistant Examiner*—Jacqueline M. Stone
*Attorney, Agent, or Firm*—Sughrue, Mion, Zinn, Macpeak & Seas

[57] ABSTRACT

A therapeutic agent for treating a hematopoietic disease containing, as an active ingredient, a glycoprotein which is recovered from human urine and acts upon the human bone marrow cells to stimulate the differentiation and proliferation of granulocytes-monocytes lineages thereof, or an active peptide fragment thereof or a derivative of said fragment, said therapeutic agent being administered after transplantation of the bone marrow.

3 Claims, No Drawings

METHOD FOR TREATING HEMATOPOIETIC DISEASES

FIELD OF THE INVENTION

This invention relates to a therapeutic agent for treating hematopoietic diseases. More particularly, it relates to a therapeutic agent for treating hematopoietic diseases containing, as an active ingredient, a glycoprotein having an activity to stimulate the differentiation and proliferation of granulocyte-monocyte progenitor cells in the human bone marrow into granulocytes or a peptide fragment thereof or a derivative of said fragment, which is to be administered after transplantation of the bone marrow for hematopoietic diseases.

BACKGROUND OF THE INVENTION

The marrow transplantation is performed on a patient suffering from a deficiency or defect in immunocompetent cells or hematopoietic cells aiming to reconstruct functions of the bone marrow by transplanting their normally functioning stem cells (the bone marrow).

Therefore, the marrow transplantation is not only applied to the treatment of primary or secondary deficiencies or defects of hematopoietic tissues or immunocompetent cells, but also, in recent years, has been widely employed in chemotherapy of malignancy for the purpose of reconstruction of those tissues or cells which are damaged together with the tumor cells as a result of the immunosuppressive therapy in expectation of more potent antitumor effects.

The diseases for which the marrow transplantation is performed include primary immunodeficiency disease, semi-aplastic anemia, hereditary progressive hemocytic functional abnormality and, in addition, tumors in the hematopoietic organs, such as acute leukemia, chronic leukemia, malignant lymphoma, plasmocytoma, progressive malignant solid tumor, etc.

Thus, the marrow transplantation is a powerful means of today for treatment of hematopoietic diseases. However, the tranplanted bone marrow cannot always perform its proper functions.

The bone marrow transplantation for a hematopoietic disease is performed when the patient is at a considerably low leucocyte level, and such a low leucocyte level is maintained for a considerably long period even after the transplantation. During this period, the patient is in danger of infectious diseases.

SUMMARY OF THE INVENTION

In order to rapidly raise a leucocyte level after the transplantation, the inventors have conducted studies on stimulation of production of granulocytes. As a result, it has now been found that administration of a specific glycoprotein, a peptide fragment thereof or a derivative of said fragment to a patient after marrow transplantation rapidly restores the leucocyte level in blood to a normal level. The present invention has been completed based on this finding.

The glycoprotein according to the present invention is recovered from human urine, acts upon the human bone marrow cells to stimulate the differentiation and proliferation of granulocytes-monocytes lineages thereof, and has the following physicochemical properties:

(a) Molecular weight: 75,000 to 90,000 (gel-filtration chromatography)

(b) Solubility: soluble in water; slightly soluble in chloroform; insoluble in ethyl alcohol or acetone (c) Specific optical rotation $[\alpha]_D^{20} = 0 \pm 40$ (0.25 w/v% aqueous solution)

(d) pH: 5.0 to 6.0 (1 w/v% aqueous solution)

(e) Isoelectric point: pH $4.7 \pm 0.2$ (f) Thermal Stability: on being heated at $60° \pm 0.5°$ C. in 1 w/v% aqueous solution, the stimulating activity on the proliferation and defferentiation of human granulocytes is completely lost at $60° \pm 0.5°$ C. for 30 minutes.

(g) Electrophoresis: The molecular weight is found to be 85,000 by sodium dodecylsulfate-polyacrylamide gel electrophoresis.

(h) Infrared absorption: characteristic absorptions at 3600–3200 (strong), 1700–1600 (strong), 1550 (medium), 1430–1380 (medium) and 1150–1000 (broad) (cm$^{-1}$).

(i) Color reaction: positive for sugars in $\alpha$-naphthol-sulfuric acid reaction, indole-sulfuric acid reaction, anthrone-sulfuric acid reaction and phenol-sulfuric acid reaction; positive for peptide linkages and amino acids in Folin-Lowry's reaction and ninhydrin reaction after hydrolysis with hydrochloric acid.

(j) Constituent amino acids in protein moiety: proline, aspartic acid, threonine, serine, glutamic acid, glycine, alanine, valine, methionine, isoleucine, leucine, tyrosine, phenylalanine, lysine, histidine, tryptophan and arginine.

(k) Color and shape: substantially white, amorphous.

(l) Constituent sugars in polysaccharide moiety: neutral sugars (on glucose conversion) = 10.0 to 13.0 w/w%; sialic acids = 3.0 to 7.0 w/w%; amino sugars = not more than 1 w/w%.

(m) Constituent of protein and polysaccharide ratio: protein = 75 to 85 w/w%; polysaccharide = 13.0 to 20.0 w/w%.

(n) Elemental Analysis: C: 42.3 to 47.3%. H: 5.7 to 7.8%. N: 9.6 to 14.3%. S: not more than 0.2%.

In the present invention, an active peptide fragment of the above-described glycoprotein or a derivative of such a fragment can also be used as an active ingredient.

DETAILED DESCRIPTION OF THE INVENTION

Processes for preparing the glycoprotein of the present invention are disclosed in Japanese Patent Application (OPI) Nos. 140707/79, 26503/80, 26504/80 and 45618/80 (the term "OPI" as herein used means "unexamined published application").

The typical process for obtaining the glycoprotein according to the present invention is as follows.

Fresh urine collected from healthy humans is adjusted to a pH 6 to 9, and preferably from 7 to 8, with a dilute acid or alkali solution, followed by centrifugation to remove any insoluble matter in the urine. The resulting supernatant is contacted with an adsorbent containing silicon, such as silica gel, silica gel-magnesium silicate, diatomaceous earth, silica glass, bentonite, etc., and the adsorbed components are eluted out preferably with an aqueous alkali solution of pH 9 or more. The aqueous alkali solution to be used as an eluent is not particularly limited, but preferably includes a 0.3 to 1.5 M aqueous solution of ammonium hydroxide, sodium hydroxide, etc. The eluate is adjusted to a pH 7 to 8, and a neutral salt, such as ammonium sulfate, is added thereto to 70% saturation to cause salting-out to thereby obtain a crude fraction containing a glycoprotein.

The resulting crude fraction is dissolved in a small amount of an aqueous alkali solution, and the solution is passed through a ultra filtration to remove low molecular weight components having a molecular weight of not greater than 10,000. The solution is then contacted with a cation-exchanger (e.g., dextran containing a carboxymethyl exchange group, carboxymethyl cellulose, phosphocellulose, etc.) to adsorb and remove impurities present in the solution. The contact is carried out under a substantially neutral condition, and the crude glycoprotein fraction and the ion exchanger are adjusted to a pH 6 to 8, preferably with a 0.01 to 0.15 M inorganic salt buffer solution. The most part of the glycoprotein having passed through the ion exchanger is concentrated and then contacted with an anion-exchanger (e.g., DEAE cellulose) equilibrated with a low salt concentration buffer solution of a pH 6 to 8 whereby the glycoprotein is adsorbed onto the anion-exchanger. The adsorbed glycoprotein is eluted with a 0.1 to 0.3 M solution of an inorganic salt, e.g., sodium chloride, with its concentration being varied (gradient elution). The glycoprotein begins to be eluted at salt concentrations of 0.1 M or higher, but complete separation is difficult. The active fractions eluted with salt concentrations of from 0.1 to 0.3 M are collected and subjected to desalting and concentration, if desired. Before the gradient elution, the glycoprotein may be previously purified by adsorption onto an anion-exchanger, followed by stepwise elution with an aqueous solution having a salt concentration of 0.3 M.

For the purpose of molecular sieve chromatography, the above fractions are passed through a column packed with a highly crosslinked polymer gel having a water absorption value of from 10 to 20 ml/g, such as Sephadex G-150, Biogel P-100, etc., and the adsorbed active ingredient is developed with a 0.05 to 0.1 M salt buffer solution. Fractions having a relative amount of the eluate of from 1.11 to 1.60, and preferably from 1.11 to 1.45, are collected, followed by desalting and concentration or lyophilizing.

The term "relative amount of eluate" means a Ve/Vo value, wherein Ve represents an amount of a solvent necessary for eluting substances within a column; and Vo represents an amount of solvent outside the gel particles within the column.

For further purification, the thus obtained crude product is dissolved in a dilute buffer solution containing 1.0 to 2.0 M of salt, e.g., a phosphate buffer solution, at a pH 6.0 to 8.0, and preferably 6.0 to 7.0, and the solution is passed through a column packed with a sugar affinitive adsorbent, e.g., concanavaline A-Sepharose 4B (sold by Pharmacia Fine Chemicals). The column is developed with a 1.0 to 2.0 M salt-containing buffer solution containing 20 to 100 mM of sugars, e.g., α-methyl-D-glucoside, etc., and having a pH 6.0 to 8.0, and preferably 6.0 to 7.0. The glycoprotein fractions are collected and, if desired, subjected to desalting, followed by concentration or lyophilization.

Further, for the purpose of electrophoretical purification, the above obtained fractions are subjected to preparative zone electrophoresis using a support, such as acrylamide gel or agarose gel at a pH 7.0 to 9.0, and the glycoprotein is recovered from the support and subjected to desalting, followed by concentration or lyophilization.

It is preferable that an aqueous solution containing the resulting glycoprotein in an amount of at least 70 mg per ml is heated at a pH 5 to 9 at a temperature of from 50° to 70° C. for a period of from 8 to 30 hours. It is more perferable to add albumin to the heat-treated glycoprotein aqueous solution as a stabilizer. The thus purified glycoprotein has a specific activity of from about 100,000 to about 1,000,000 units/mg.

The glycoprotein recovered from human urine by the above-described process is lyophilized in a vial under sterile conditions and sealed in a powder form. Prior to the lyophilization, human serum albumin as a stabilizer for the glycoprotein and an amino acid or a saccharide as an aid for reconstitution may be added to the glycoprotein, followed by sterile filtration.

Determination of the biological activity of the glycoprotein can be carried out by taking the colony formation of mouse bone marrow cells in vitro as a parameter. Specifically, 0.1 ml of a sample is mixed with 1 ml of McCoy's 5A medium containing 20% fetal bovine serum, 0.3% agar and $7.5 \times 10^4$ of mouse bone marrow cells in a plastic dish of 35 mm in diameter. The culture dishes are incubated at 37° C. for 7 days in humidified air containing 5% $CO_2$. After incubation, colonies composed of 50 or more cells are counted under an inverted microscope, and one colony formed is represented as one unit.

In the present invention, a peptide fragment having the stimulating activity on the differentiation and proliferation of granulocyte obtained from the above-described glycoprotein or a derivative of such a peptide fragment can also be used as an active ingredient. Fragmentation can be carried out by deglycosylation or dissociation treatment with known enzymes. Peptide fragments having a stimulating activity on differentiation and proliferation of granulocyte which are derived from recombinant product may also be utilized.

The preparations according to the present invention are dissolved in, e.g., physiological saline, and/or distilled water, for injection, etc., at a concentration of from 10 to 100 mg/ml and administered by drip infusion or direct intravenous, intramuscular or subcutaneous injection.

The dosage usually ranges from 1,000 to 150,000 units/Kg body per dose but is subject to variation according to symptoms.

The time of administration is immediately after the marrow transplantation or 3 to 10 days after the marrow transplantation, at which the leucocyte level does not reach the normal value or a GVH (graft vs host) reaction to the implant seems to occur. The administration may be conducted several times or maintained for several days (2 to 14 days) according to a variation in a leucocyte level until it becomes constant.

Patients to be treated with the preparations of the present invention are not particularly limited as far as they suffer from hematopoietic diseases and have been transplanted with the bone marrow.

When the preparations according to the present invention are administered to the above-mentioned patients, a marked improvement in the leucocyte level in blood was noted without being accompanied by any harmful side effects, thus suggesting usefulness of the preparations as treating agents for hematopoietic diseases.

The present invention will now be described in greater detail by way of Example and Test Examples, but it should be understood that these examples are not intended to limit the present invention.

EXAMPLE 1

Fresh urine (400 l) collected from healthy persons was adjusted to a pH 8 with 10% sodium hydroxide and then subjected to centrifugation at 15,000 rpm while cooling to 0° C. to thereby remove any insoluble matter. The resulting supernatant was ajdusted to a pH 7 with 10% hydrochloric acid and passed through a column (10×80 cm) packed with silica gel. The component adsorbed onto silica gel was eluted with 40 to 5% aqueous ammonia. The eluate was ajdusted to a pH 7.5 with 1N sulfuric acid, and ammonium sulfate was added thereto to 70% saturation. The solution was allowed to stand at 0° C. overnight, and the formed precipitate was collected by centrifugation. The precipitate was dissolved in 2l of 5% aqueous ammonia, and the solution was sufficiently dialyzed in a cellulose tubing (manufactured by Visking Co.) against a 0.05 M phosphate buffer solution (pH 6.5). To the non-dialyzed liquid was added the same buffer solution to make 10 liters. The solution was passed through a column (4.0×40 cm) packed with a CM Sephadex C-50 ion exchanger previously equilibrated with a 0.05 M phosphate buffer solution (pH 6.5) to adsorb impurities onto the ion exchanger.

The effluent (10 l) was concentrated by Diaflow hollow fiber concentrating apparatus (DO-30 Model, manufactured by Amicon Co., Ltd.), and the concentrate was subjected to dialysis against a 0.1 M tris-HCl buffer solution (pH 7.0) at 5° C. overnight in the same manner as described above. The same buffer solution was added to the non-dialyzed liquid to make 3 liters.

The resulting solution was passed through a column (4.0×40 cm) of DEAE cellulose which had been activated and equilibrated with the same buffer solution. After thoroughly washing the column with a 0.1 M tris-HCl buffer solution (pH 7.0), the column was eluted with a 0.1 M tris-HCl buffer solution (pH 7.0) containing 0.3 M sodium chloride. Fractions having a stimulating activity on the differentiation and proliferation of granulocyte were collected and dialyzed against a 0.1 M tris-HCl buffer solution (pH 7.0).

The non-dialyzed liquid was again passed through a column (4.0×40 cm) of DEAE cellulose which had been equilibrated with the same buffer solution and eluted with a linear concentration gradient of from 0.1 to 0.3 M NaCl. Fractions having a stimulating activity on differentiation and proliferation of granulocyte were collected, and ammonium sulfate was added thereto to 70% saturation. The precipitate thus formed was collected, dissolved in a small amount of a 0.1 M tris-HCl buffer solution (pH 7.0) and dialyzed against the same buffer solution.

The non-dialyzed liquid (20 ml) was applied to a column (4.0×60 cm) pakced with Sephadex G-150 previously equilibrated with a 0.1 M tris-HCl buffer solution (pH 7.0). Fractions having a relative amount of eluate of from 1.11 to 1.45 were collected and thoroughly dialyzed against distilled water. The non-dialyzed liquid was lyophilized to obtain about 500 mg of a powder.

The resulting powder (200 mg) was dissolved in a 0.02 M phosphate buffer solution (pH 7.0) containing 1.0 M sodium chloride, and the solution was passed through a column containing 100 ml of concanavalin A-Sepharose 4B (produced by Pharmacia Fine Chemicals) which had been equilibrated with the same buffer solution. The column was thoroughly washed with a 0.02 M phosphate buffer solution (pH 7.0) containing 1.0 M sodium chloride and then eluted with a 0.02 M phosphate buffer solution (pH 7.0) containing 50 mM α-methyl-D-glucoside and 1.0 M sodium chloride. Fractions having a stimulating activity on the differentiation and proliferation of granulocyte as assayed by the method as described above were collected and subjected to dialysis against distilled water. The non-dialyzed liquid was freeze-dried.

About 50 mg of the resulting freeze-dried powder ws dissolved in 1 ml of a 0.125 M tris-HCl buffer solution (pH 6.8) containing 10% glycerol, and the solution was subjected to zone electrophoresis at 10 mA therethrough under water-cooling by means of an apparatus for preparative electrophoresis (Unifor 7,900 Model, produced by LKB) using 8% acrylamide gel (pH 8.9; 25 mm×100 mm). A fraction having a relative mobility of 0.46 was recovered and dialyzed against distilled water. Lyophilization of the non-dialyzed liquid gave about 10 mg of a glycoprotein according to the present invention.

The above procedure was repeated to obtain about 1 g of the purified glycoprotein. To 1 g of the thus purified glycoprotein was added 10 ml of water to completely dissolve the glycoprotein, and an aqueous 10% sodium hydroxide solution was added thereto to adjust to a pH 6.8.

The resulting solution was heated at 60° C. for 10 hours, followed by quenching with ice-water. The solution was 10-fold diluted with sterilized water, filtered through a membrane filter having a pore size of 0.45 μm (produced by Millipore) to remove bacteria, sterilely poured into vials which had previously been dry-sterilized at 180° C. for 2 hours in 1 ml portions, aseptically lyophilized and sealed to obtain about 97 vials each containing 1 mg of the heat-treated glycoprotein.

EXAMPLE 2

From 1,000 l of fresh urine collection from healthy persons, 2.5 l of an aqueous solution containing a crude glycoprotein was obtained in the same manner as described in Example 1. To the aqueous solution was added 25 l of a 0.1 M tris-HCl buffer solution (pH 7.0), and the solution was thoroughly stirred, followed by concentration to about 1/25 time the volume by the use of a Diaflow hollow fiber concentration apparatus. To the concentrate were added 5 l of a 0.1 M tris-HC buffer solution (pH 7.0) and 5 l of a DEAE cellulose solution (dry DEAE cellulose content: 200 g) equilibrated with a 0.1 M tris-HCl buffer solution (pH 7.0). After stirring for 30 minutes, the mixture was allowed to stand and then filtered by suction to separate the cellulose. The cellulose was washed with 10 of a 0.1M tris-HCl buffer solution (pH 7.0) and again filtered by suction to separate the cellulose. The separated cellulose was washed with 10 of a 0.1 M tris-HCl buffer solution (pH 7.0) containing 0.05 M sodium chloride, followed by filtration by suction to separate the cellulose. To the separated cellulose was added 10 of a 0.1 M tris-HCl buffer solution (pH 7.0) containing 0.3 M sodium chloride, followed by stirring to elute the glycoprotein from the DEAE cellulose. The resulting eluate was repeatedly diluted with distilled water followed by concentration on use of a Diaflow hollow fiber concentration apparatus (DC-30 Model). The concentrate was desalted and lyophilized to obtain about 15 g of a powder. The resulting lyophilized powder was dissolved in 150 ml of distilled water, and the solution was applied to a gel filtration column (6.0×80 cm) packed with Sephadex G-150 equilibrated with a 0.1 M tris-HCl buffer solution (pH 7.0). Glycoprotein-containing fractions having relative amounts of eluate of from 1.11 to 1.60 were collected and thoroughly dialyzed against distilled water. The non-dialyzed liquid was concentrated by means of a Diaflow hollow fiber concentration apparatus (DC 2 Model) to obtain 100 ml of a concentrate containing about 9 g of a crude glycoprotein. The concentrate was adjusted to a pH 6.1 with a 0.1 M sodium phosphate buffer solution and then heated in the same manner as in Example 1. After filtration to remove bacteria, the solution was poured into vials in 2.5 ml portions, freeze-dried and sealed under a sterile condition to obtain 40 vials each containing about 3.8 mg of the heat-treated glycoprotein.

TEST EXAMPLE 1

Acute toxicity of the glycoprotein prepared in Example 1 was determined in $C_{57}BL$ male mice by the method of Richard et al., *Journal of Pharmacology and Experimental Therapeutics*, 90, 99 (1949). The results obtained are shown in Table 1 below.

TABLE 1

| Administration Route | $LD_{50}$ |
|---|---|
| i.p. | $1 \times 10^8$ unit/Kg (100 mg/Kg) |
| i.v. | $5 \times 10^7$ unit/Kg (50 mg/Kg) |
| s.c. | $1 \times 10^8$ unit/Kg (100 mg/Kg) |

TEST EXAMPLE 2

A patient who suffered from acute lymphatic leukaemia underwent transplantation of the marrow on September 12. An intravenous drip infusion with 4,000,000 unit per day of a glycoprotein was then given for consecutive 7 days from September 20. Before the marrow transplantation, the patient received radiation thereapy with 200 rad in total for 4 days from September 5 to 8 and administration of Endoxan at a total does of 2,500 mg for 2 days from September 7 to 8. A variation in leucocyte and granulocyte levels in blood with time during these periods is shown in Table 2.

TABLE 2

| Month/Day | Number of Leucocyte (/mm³) | Number of Granulocyte (/mm³) |
|---|---|---|
| 9/5 | 2170 | 911 |
| 8 | 2240 | 1857 |
| 10 | 1060 | 986 |
| 12 | 540 | 491 |
| 14 | 320 | |
| 17 | 70 | |
| 19 | 130 | |
| 21 | 90 | |
| 25 | 3310 | 166 |
| 26 | 1770 | 212 |
| 27 | 900 | 128 |
| 29 | 1210 | 157 |
| 10/1 | 2040 | 204 |
| 3 | 3160 | 343 |
| 5 | 2200 | 572 |
| 8 | 2150 | 366 |
| 11 | 2560 | 589 |
| 10/13 | 2430 | 1021 |
| 15 | 2810 | 899 |
| 17 | 3340 | 1303 |
| 19 | 3430 | 1989 |
| 22 | 4430 | 3278 |
| 24 | 5290 | 3756 |

While the invention has been described in detail and with reference to specific embodiments thereof, it will be apparent to one skilled in the art that various changes and modifications can be made therein without departing from the spirit and scope thereof.

What is claimed is:

1. In a process in which bone marrow is tranplanted in a patient being treated for hematopoietic disease, the improvement which comprises administering to said patient immediately after said bone marrow transplantation or 3 to 10 days after said marrow transplantation for 2 to 14 consecutive days, in a dose ranging from 1,000 to 150,000 units/kg body weight, a glycoprotein which is recovered from human urine and acts upon the human bone marrow cells to stimulate the differentiation and proliferation of granulocytes-monocytes and lineages thereof and wherein said glycoprotein has the following physiochemical properties:
   (a) Molecular weight: 75,000 to 90,000 as determined by gel filtration chromatography and 85,000 as determined by sodium dodecylsulfate-polyacrylamide gel electrophoresis,
   (b) pH: 5.0 to 6.0 (1 wt% aqueous solution),
   (c) Color reaction: positive for sugars in α-naphthol-sulfuric acid reaction, indole-sulfuric acid reaction, anthrone-sulfuric acid reaction and phenol-sulfuric acid reaction; positive for peptide linkages and amino acids in Folin-Lowry's reaction and ninhydrin reaction after hydrolysis with hydrochloric acid,
   (d) Constituent amino acids in protein moiety: proline, aspartic acid, threonine, serine, glutamic acid, glycine, alanine, valine, methionine, isoleucine, leucine, tyrosine, phenylalanine, lysine, histidine, tryptophan and arginine, and
   (e) Color and shape: substantially white, amorphous.

2. The process of claim 1, wherein the glycoprotein has the following additional physiochemical properties:
   (a) Solubility: soluble in water; slightly soluble in chloroform; insoluble in ethyl alcohol or acetone,
   (b) Specific optical rotation: $[\alpha]_D^{20}=0\pm40$ (0.25% aqueous solution),
   (c) Constituent sugars in polysaccharide moiety: neutral sugars (on glucose conversion)=10.0 to 13.0 w/w%; sialic acids=3.0 to 7.0 w/w%; amino sugars=not more than 1 w/w%, and
   (d) Elementary Analysis: C: 42.3 to 47.3%; H: 5.7 to 7.8%; N: 9.6 to 14.3%; S: not more than 0.2%.

3. The process of claim 1, wherein the glycoprotein has the following additional physicochemical properties:
   (a) Solubility: soluble in water; slightly soluble in chloroform; insoluble in ethyl alcohol or acetone,
   (b) Specific optical rotation: $[\alpha]_D^{20}=0\pm40$ (0.25% aqueous solution),
   (c) Isoelectric point: pH 4.7±0.2,
   (d) Thermal stability: on being heated at 60°±0.5° C. in 1% (w/v) aqueous solution, the stimulating activity on the proliferation and differentiation of human granulocytes is completely lost,
   (e) Infrared absorption: characteristic absorptions at 3600–3200 (strong), 1700–1600 (strong), 1550 (medium), 1430–1380 (medium) and 1150–1000 (broad) (cm$^{-1}$),
   (f) Constituent sugars in polysaccharide moiety: neutral sugars (on glucose conversion)=10.0 to 13.0 w/w%; sialic acids=3.0 to 7.0 w/w%; amino sugars=not more than 1 w/w%,
   (g) Constituent protein and polysaccharide ratio: protein=75 to 85 w/w%; glucide=13.0 to 20.0 w/w%,
   (h) Elementary Analysis: C: 42.3 to 47.3%; H: 5.7 to 7.8%; N: 9.6 to 14.3%; S: not more than 0.2%.

* * * * *